United States Patent [19]
Benet et al.

[11] Patent Number: 4,726,931
[45] Date of Patent: Feb. 23, 1988

[54] APPARATUS FOR WITHDRAWING LIQUID SAMPLES

[75] Inventors: Robert Benet; Maurice Jouannic, both of Grand Quevilly, France

[73] Assignee: Rhone-Poulenc Chimie de Base, Courbevoie, France

[21] Appl. No.: 627,835

[22] Filed: Jul. 5, 1984

[30] Foreign Application Priority Data

Jul. 5, 1983 [FR] France ................................. 83 11141

[51] Int. Cl.⁴ ...................... B01D 29/00; G01N 1/10; G01N 35/08
[52] U.S. Cl. .................................. 422/81; 73/863.23; 210/96.1; 210/253; 210/745; 422/62; 422/101; 422/119; 436/55
[58] Field of Search .................. 422/81, 101, 62, 111, 422/119; 210/96.1, 294, 253, 101, 739, 745, 418; 73/863.23, 863.24, 864.34, 864.35, 863.83; 436/50, 55

[56] References Cited

U.S. PATENT DOCUMENTS

| | | | |
|---|---|---|---|
| 2,204,225 | 6/1940 | Merckel | 210/745 |
| 3,561,273 | 2/1971 | Tanila | 73/863.23 |
| 3,834,588 | 9/1974 | Jones | 222/61 |
| 4,052,161 | 10/1977 | Atwood et al. | 210/81 |
| 4,116,832 | 9/1978 | Tardivel | 210/96.1 |
| 4,323,537 | 4/1982 | Mody | 422/63 |

FOREIGN PATENT DOCUMENTS

| | | | |
|---|---|---|---|
| 683028 | 10/1939 | Fed. Rep. of Germany | 422/101 |
| 2067416 | 8/1971 | France | |
| 2317002 | 2/1977 | France | |
| 1175966 | 1/1970 | United Kingdom | 422/62 |

Primary Examiner—Barry S. Richman
Assistant Examiner—C. M. Delahunty
Attorney, Agent, or Firm—Burns, Doane, Swecker & Mathis

[57] ABSTRACT

Apparatus for withdrawing liquid samples from liquid/solids media, e.g., phosphoric acid slurries, for the downstream analysis thereof, is comprised of (i) means adapted for insertion into a liquid/solids medium to selectively separate and receive a liquid fraction therefrom, (ii) a liquid storage first chamber in communicating relationship with said separating and receiving means (i), (iii) a liquid sample receiving second chamber in independent, parallel communicating relationship with said separating and receiving means (i) and which comprises means for exteriorly discharging sample contained therein, and (iv) means permitting the filling or emptying of said second chamber (iii) independently of said first chamber (ii).

20 Claims, 5 Drawing Figures

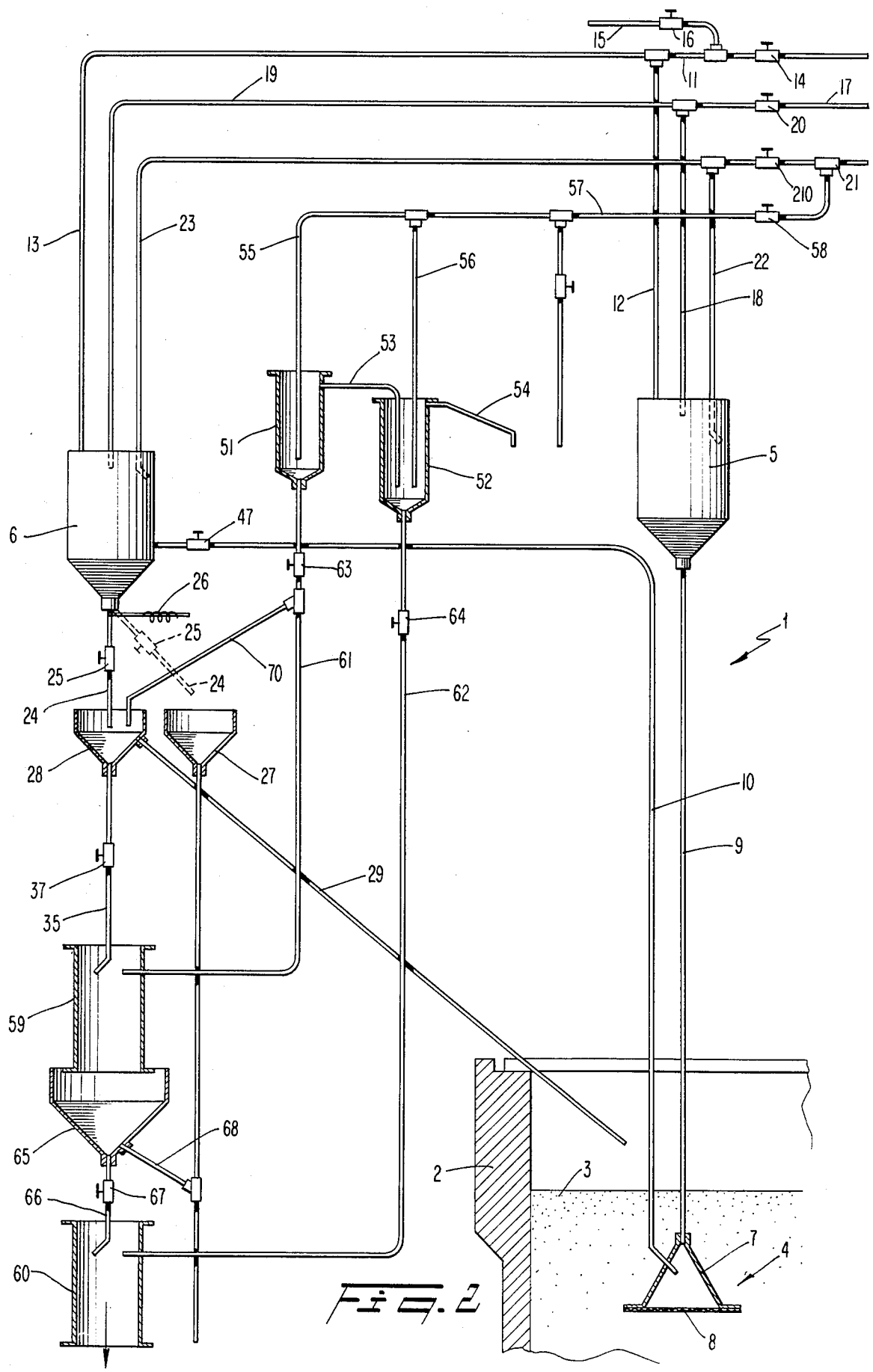

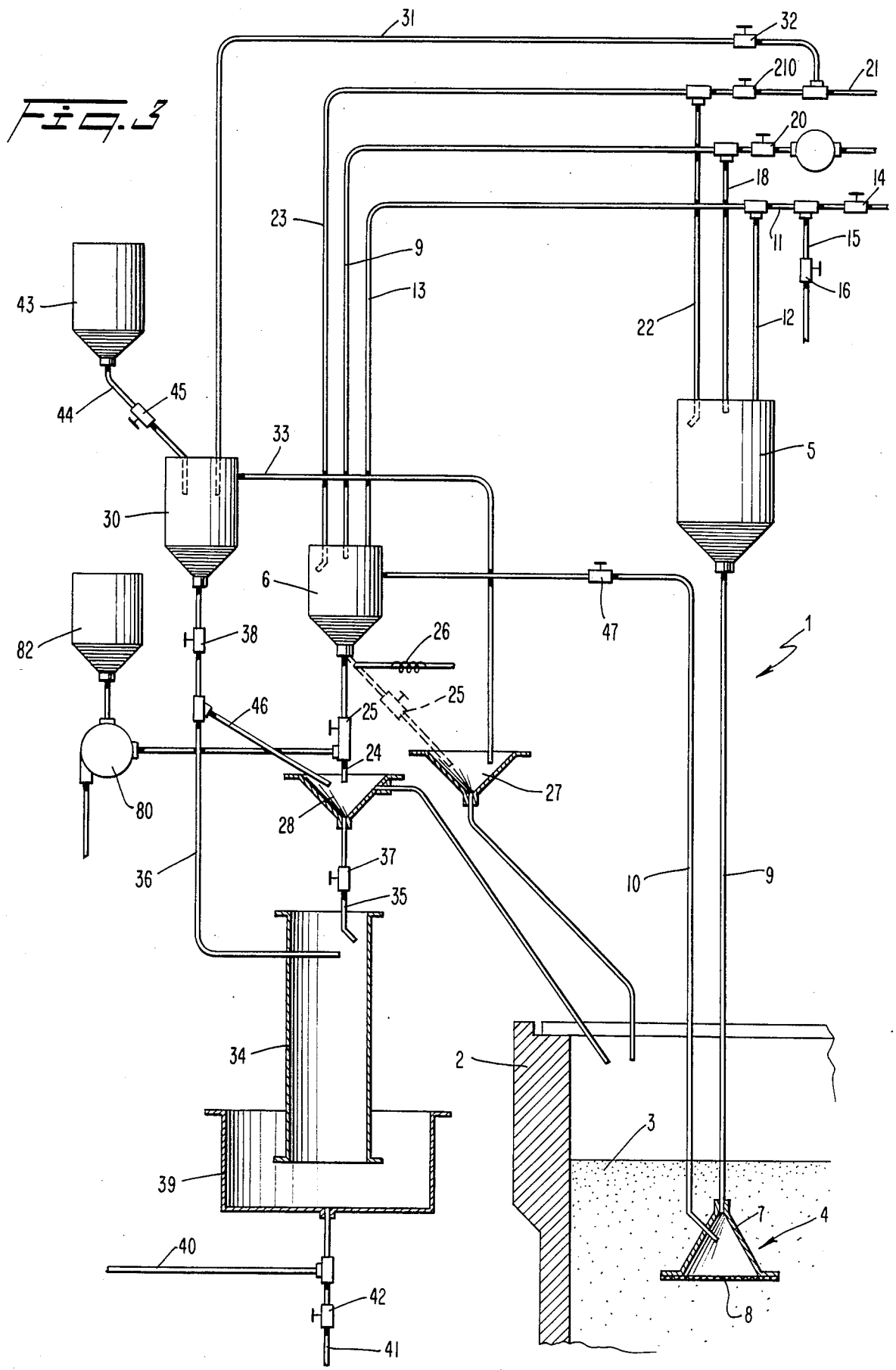

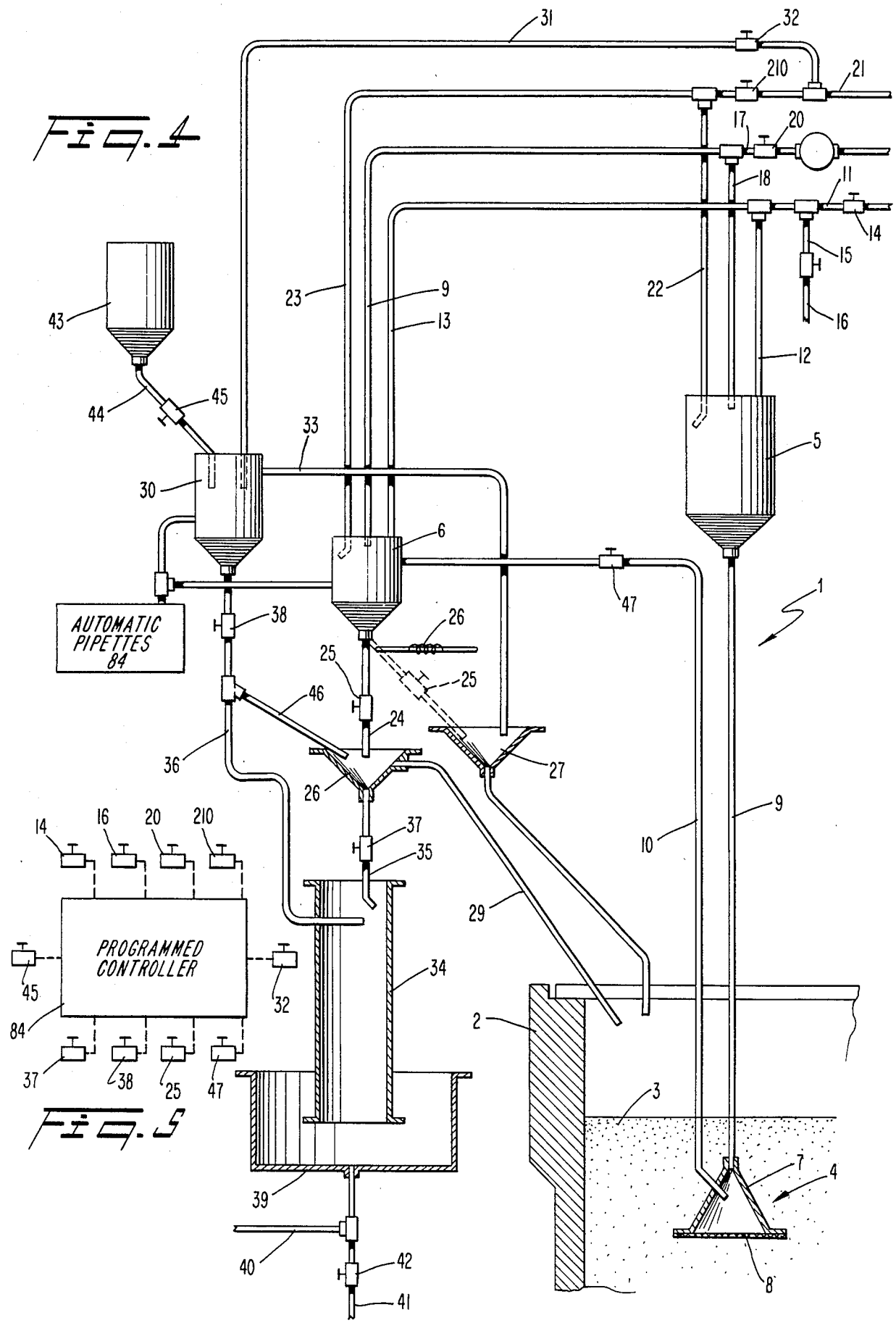

APPARATUS FOR WITHDRAWING LIQUID SAMPLES

BACKGROUND OF THE INVENTION

1. Field of the Invention

The present invention relates to apparatus for the taking of liquid samples from a mixture of liquid and solids.

2. Description of the Prior Art

The chemical industry in particular is often involved with processes which use reaction media comprised of a mixture of liquid and solid. In such cases, it is often a matter of interest to be able to analyze the liquid phase of the mixture in such manner as to be able to trace the progress of the reaction, or to be able to control the reaction.

A typical example is the production of phosphoric acid by a wet process, wherein the phosphate ore is subjected to attack by a strong acid. In the case of an attack sequence using sulfuric acid, the resulting product is a slurry including a liquid phase which comprises, in particular, the product phosphoric acid, and a solid phase which contains, in particular, calcium sulfate.

Now, in order to ensure that the reaction takes place in a satisfactory manner, it is very important to maintain the content of sulfate ions in the reaction medium within a well defined range. For that purpose, it is therefore necessary to ascertain the concentration of sulfate ions quickly and as frequently as may be required.

French Patent No. 2,090,541 describes apparatus for the automatic continuous analysis of the $H_2SO_4$ in phosphoric acid, which operates on the strong acid resulting from filtration of the attack slurry.

The disadvantage of such an apparatus is precisely in the fact that it analyzes an acid resulting from the filtration operation. Indeed, it is highly probable that analysis carried out utilizing such apparatus does not precisely reflect the conditions prevailing in the attack vessel. Thus, in the filtration operation, various phenomena may occur, which modify the composition of the acid. Moreover, it is preferable to analyze the acid directly within the attack vessel rather than at the outlet of the filter to provide a much shorter response time, thus affording the possibility of immediate intervention, if needed.

However, it has been found to be difficult to develop an apparatus for the taking of samples of acid directly from the reaction medium, for the purpose of effecting the analysis thereof. In fact, to be suitable for industrial use, such an apparatus must be adapted to resist corrosion, it must operate without requiring frequent cleaning and therefore it must be so designed as not to be rapidly fouled by the attack slurry. In addition, the liquid sample must be as free from any solid impurity as possible, in order to avoid problems in carrying out any analysis.

SUMMARY OF THE INVENTION

Accordingly, a major object of the present invention is the provision of a simple yet reliable apparatus comprising means for withdrawing a liquid sample from a slurry or mixture of liquid and solids for the purpose of downstream analysis thereof.

Briefly, the apparatus according to this invention comprises:

(i) means for filtering said mixture and receiving the filtered liquid;

(ii) a first liquid storage chamber which is connected by a first conduit to said filtering and receiving means;

(iii) a second chamber for receiving the liquid sample which is connected in parallel with respect to the first chamber by a second conduit to said filtering and receiving means, and which is provided with means for discharging the stored sample to the exterior; and (iv) a closure member disposed along the second conduit to permit filling or emptying of the second chamber independently of the first chamber.

In preferred alternative embodiments of the invention, the aforementioned chambers are connected, in a manner which either may or may not be independent, to a vacuum source by means of a circuit comprising at least one closure or valve member. Likewise, they may be connected whether independently or not, to a water supply and/or to an air supply by means of circuits which respectively comprise at least one closure member.

In addition, the apparatus according to the invention may comprise means for diluting the liquid sample which is discharged from the second chamber, said means comprising:

(1) a first calibrated receptacle for receiving the liquid discharged from the second chamber;

(2) one or more mixing containers which are arranged in series, into which, or into the first of which, said first receptacle discharges, and discharging into a receiving container;

(3) a second or, in the case where there is a plurality of mixing containers, a series of second calibrated receptacles which are arranged in parallel and which are connected by way of a circuit to a water supply and which each discharge into a respective mixing container; and (4) closure members in the water supply circuit of the second receptacle or the series of second receptacles and in each of the connecting conduits between the receptacle or receptacles and the mixing container or containers and between same.

Having regard to its simplicity, the apparatus according to the invention can operate without requiring frequent cleaning operations. In addition, by virtue of its structure, it makes it possible to supply the analyzer with a particularly clean liquid sample, namely, a sample devoid of solid impurities.

BRIEF DESCRIPTION OF THE DRAWINGS

FIG. 2 is a schematic/diagrammatic illustration of a second embodiment of apparatus according to the invention, also including dilution means.

FIG. 3 is a schematic/diagrammatic illustration of the embodiment of FIG. 1 with the addition of a peristaltic pump;

FIG. 4 is a schematic/diagrammatic illustration of the embodiment of FIG. 1 with the addition of automatic pipettes; and FIG. 5 is a schematic of a programmed controller suitable for use with the embodiment of FIG. 1.

DETAILED DESCRIPTION OF THE INVENTION

Figure 1:
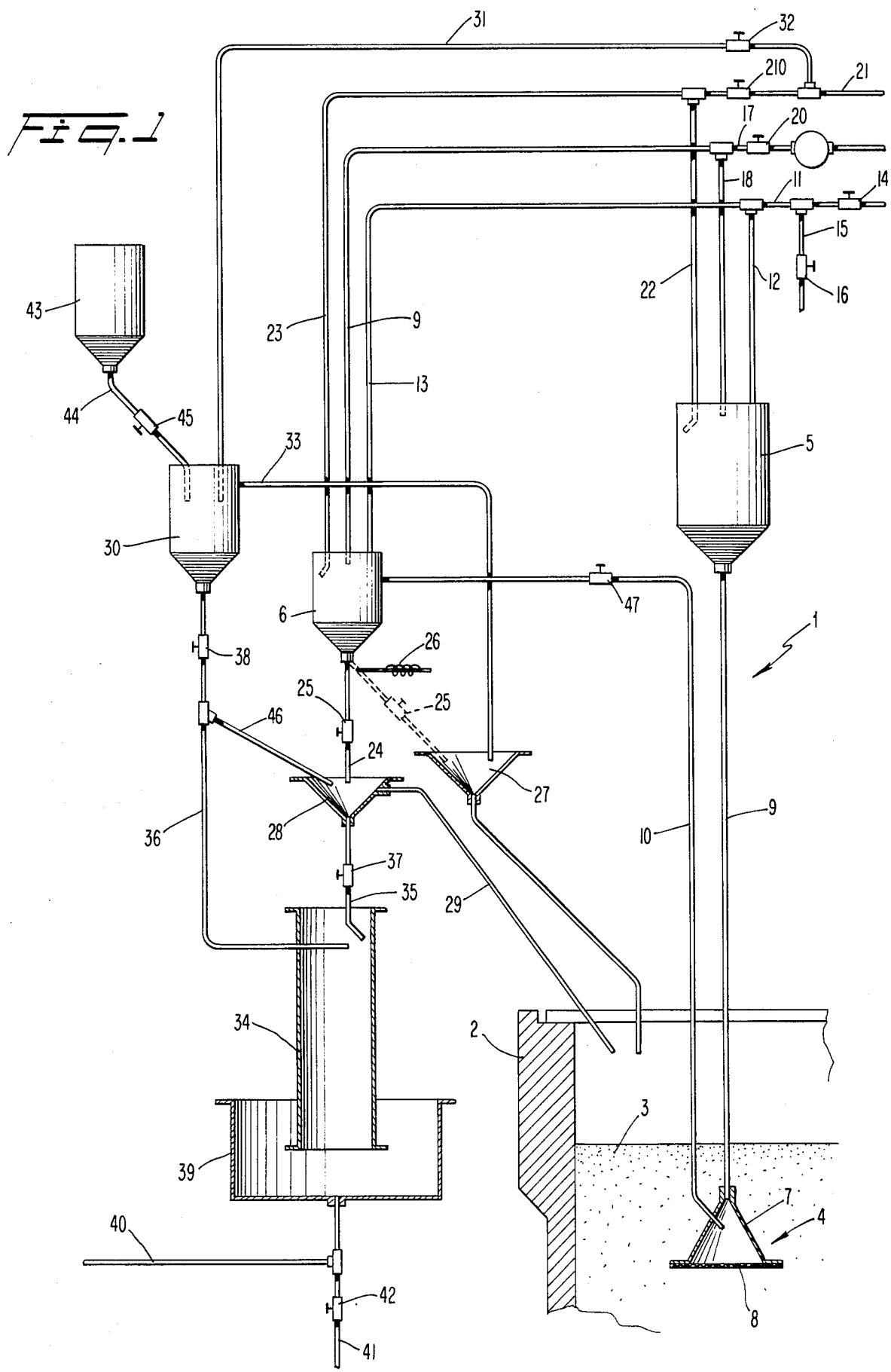
FIG. 1 is a schematic/diagrammatic illustration of one embodiment of apparatus according to the invention, including dilution means.

In the description which follows, the subject apparatus is illustrated in the context of a wet process for the production of phosphoric acid. It is readily apparent, however, that such apparatus is equally applicable to any other chemical process giving rise to a liquid reaction mixture charged with solid material, whether to greater or lesser degree.

More particularly, and with reference to FIG. 1 of the Drawings, the apparatus 1 according to the invention is shown mounted upon an attack vessel or tank 2 containing a slurry 3 comprising, in particular, a mixture of phosphate, phosphoric acid, sulfuric acid and calcium sulfate.

The sampling apparatus 1 essentially comprises means 4 for filtering the mixture and receiving the filtered liquid, and two chambers 5 and 6 for storing the filtered liquid.

The means 4 may be of any suitable structure. For the embodiment illustrated, which is especially suitable in the context of a process for the production of phosphoric acid, the means 4 (which will be hereinafter referred to as the "filter") comprises a conical container 7, the base of which is provided with a filtering element 8. The filtering element 8 may be, for example, a filter cloth of the type conventionally used for attack slurry filters. The cloth or more generally the filtering element 8 may be secured to the container 7 by any suitable means and may occupy only a part or the entirety of the base thereof. The assembly of the container and the filtering element is preferably immersed in the slurry 3 to a greater or lesser depth.

The first storage chamber 5 is connected by a conduit 9 to the filter 4, and the second chamber 6 by a conduit 10 provided with a closure member 47, e.g., an electrically operated valve. Hereinafter in this description, reference will be made to an electrically operated valve, but it is apparent that any other similar closure or shut-off member may be used. In an important embodiment of the invention, the two chambers 5 and 6 are therefore each separately series arranged in with respect to the filter 4 and are parallel to each other, and the filtrate thus cannot pass directly and successively from the filter to the chamber 5 and then to the chamber 6. In the illustrated construction, the conduits 9 and 10 are completely separate. They could possibly have a common portion. For the type of filter illustrated, it is advantageous for the conduit 9 from the first chamber 5 to be connected to the filter 4 at the top of the conical container 7 or in the near vicinity thereof, with the conduit 10 from the other chamber 6 communicating with the filter in the immediate vicinity of the filtering element 8.

Preferably, the chambers 5 and 6 are cylindrical and are provided with a conical bottom portion. Conduits 11, 12 and 13 connect the chambers 5 and 6 to a vacuum source (not shown). The conduit 11 is provided with an electrically operated valve 14.

A tap 15 on the conduit 11, which is provided with a valve 16, permits the vacuum to be broken.

In addition, conduits 17, 18 and 19 connect the chambers 5 and 6 to a compressed air source (not shown), the intake of air into the conduit 17 being controlled by a valve 20.

Furthermore, conduits 21, 22 and 23 connect the chambers 5 and 6 to a water intake (not shown). An electrically operated valve 210 is provided along the conduit 21. It will be noted that the water conduits 22 and 23 are so disposed as to open into the chambers tangentially with respect to the walls thereof. In the preferred construction where the chambers are cylindrical, that arrangement of the conduits permits the water to flow into the chambers in a cyclonic motion.

A conduit 24 provided with a valve 25 permits the contents of the chamber 6 to be discharged therefrom. The conduit 24 may be flexibly mounted in such manner that it can assume two positions under the action of a control mechanism 26 of solenoid type. In the first direction, the conduit 24 discharges towards the exterior of the system in the direction of an analyzer, optionally by way of dilution means more fully described hereinafter.

In the second position, the conduit 24 discharges into a receptacle 27 which discharges the liquid to waste or which returns it to the mixture to be analyzed, for example, into the attack vessel.

Depending upon the type of analyzer used, it may be necessary to dilute the sample collected by the sampling apparatus to a greater or lesser degree. In addition, in the particular case of phosphoric acid, such dilution may prevent the formation of solid deposits, in particular fluosilicates, and it should be carried out as quickly as possible. It is for that reason that the apparatus according to the invention may include sample diluting means, which will now be described.

The sample diluting means first comprise a receptacle 28 which is very precisely calibrated and which is provided with an overflow 29 for discharging the excess contents thereof, which overflow may discharge, for example, into the attack vessel. It is into the receptacle 28 that the discharge conduit 24 of the chamber 6 discharges, in the first position thereof.

The diluting means also comprise a second receptacle 30 which is also very precisely calibrated and which is connected by a conduit 31 provided with an electrically operated valve 32 to the water source. The receptacle 30 is provided with an overflow 33 which opens, for example, into the receptacle 27. The receptacle 30 is preferably cylindrical and provided with a conical bottom.

The receptacles 28 and 30 are connected to a mixer tube 34 by way of conduits 35 and 36, respectively, each of which is provided with a respective electrically operated valve 37 and 38. Preferably, the conduits 35 and 36 are so arranged as to open into said tube 34 tangentially (with respect to the wall of the mixer tube). A branch conduit 46 is provided along the conduit 36, which opens into the receptacle 28.

The mixer tube 34 opens into a receiving container 39 which is connected by a conduit 40 to the analyzer (not shown) and by a conduit 41 provided with an electrically operated valve 42 to the drain, or waste.

The analyzer which in and of itself does not constitute an object of the present invention may be of any known type and is of course adapted to the sample withdrawn.

Finally, it is possible to provide a tank or reservoir 43 for a cleaning liquid, for example, nitric acid when the apparatus is used for the production of phosphoric acid. The tank 43 communicates with the receptacle 30 by way of a conduit 44 provided with an electrically operated valve 45.

The various electrically operated valves are advantageously actuated by a programmer (not shown).

The apparatus shown in FIG. 1 operates in the following manner:

The filter 4 is immersed in the vessel and the chamber 5 is placed under vacuum by opening the valve 14. The other valves are closed, in particular the valve 47.

Due to the suction intake effect, a cake, for example, of gypsum, is formed under the filter cloth 8. Acid passes into the container 7 and fills the chamber 5. The acid is dirty, at least at the beginning of the operation. After a certain period of time has elapsed, the cake itself acts as a filter and the acid which is drawn in becomes clean. At that moment, the valve 47 is opened and a given volume of acid is drawn into the chamber 6. That clean acid constitutes the sample intended for analysis.

The valves 14 and 47 are then closed, the valves 16 and 25 are opened and the vacuum is cut off. The acid contained in the chamber 5 is discharged towards the filter 4 and passes through the cloth 8, detaching the cake therefrom. The sample flows through line 24 into the receptacle 28 and is diluted in accordance with a process to be described hereinafter.

The valves 210 and 47 are then opened and hot water under pressure washes the chambers 5 and 6 and the conduits 9 and 10. During that time, the conduit 24 is moved by means 26 into a position (shown by the dashed line) such as to discharge into the receptacle 27 so as to permit the rinsing liquid collected at the bottom of the chamber 6 to be discharged.

Finally, after the valve 210 is closed, the valve 20 is opened and compressed air is charged into the chambers 5 and 6 and the conduits 9 and 10. That air expels the last traces of water and, by pressuring the remaining water to pass through the filter cloth, unclogs the cloth.

The sampling cycle proper is concluded. The valves 20 and 47 are closed and the valve 14 is opened, thus permitting another sample to be withdrawn.

Subsequent to or simultaneously with the sampling cycle, a cycle for diluting the sample takes place, which will now be described. In the sequence described, the system permits dilution to one tenth. It will be apparent that any other dilution value may be selected, by modifying the volumes of liquid used.

The sample contained in the chamber 6 is discharged into a receptacle 28 which is very precisely calibrated at a volume of 50 cm$^3$. The overflow amount is discharged by way of the overflow means 29.

In addition, by the valve 32 being opened for a fixed period of time, the receptacle 30 which is very precisely calibrated at 450 cm$^3$ is filled. The water which is transferred into the receptacle 30 also receives a slight make-up amount of nitric acid from the tank 43 after the valve 45 is opened. Any overflow amount in the receptacle 30 flows away through line 33.

The valves 37 and 38 are then opened simultaneously and the liquids contained in the receptacles 28 and 30 are mixed in the course of their cyclonic movement in the mixer 34. The resulting mixture is collected in the container 39. A small amount of water also flows through the branch conduit 46 which permits the receptacle 28 to be washed. Having regard to the volumes used, the mixture produced represents dilution of the sample taken to one tenth, the required amount of dilute sample then being conveyed to the analyzer by way of the conduit 40. Any residual sample is discharged by way of conduit 41 after opening of the valve 42.

The apparatus shown in FIG. 2 differs from that shown in FIG. 1 only in regard to the dilution cycle thereof, which is somewhat more complex. It permits dilution to one hundredth. In consequence, the same components of the sampling part of the apparatus are denoted by the same reference numerals as those used in FIG. 1, and such components will not again be described.

The diluting apparatus comprises two receptacles 51 and 52 which are very precisely calibrated at 450 cm$^3$. An overflow 53 communicates the receptacle 51 with the receptacle 52, the latter being provided with an overflow 54 which can discharge, for example, into the receptacle 27. The receptacles 51 and 52 are connected to the water supply by way of conduits 55, 56 and 57, the latter being provided with a valve 58.

In addition, two mixer tubes 59 and 60 are arranged in series, with the calibrated receptacle 28 discharging into the tube 59. The receptacles 51 and 52 each discharge into a mixer tube 59 and 60, respectively, by way of conduits 61 and 62 which are each fitted with an electrically operated valve 63 and 64, respectively. A branch conduit 70 can connect the receptacles 51 and 28.

A receptacle 65 which is precisely calibrated at 50 cm$^3$ is positioned between the tubes 59 and 60. The tube 59 discharges directly therein and the receptacle 65 discharges into the tube 60 by way of the conduit 66 which is fitted with an electrically operated valve 67. The receptacle 65 is also provided with an overflow 68 which discharges down the drain or to waste, or possibly to the attack vessel.

The same components as those described in relation to the apparatus shown in FIG. 1 may also be provided at the discharge of the tube 60.

It will be appreciated that it is possible to provide a cleaning liquid tank or reservoir, as in the construction shown in FIG. 1.

The immediately aforedescribed diluting apparatus operates in the following manner:

The receptacles 51 and 52 are filled by opening the valve 58. Then, a first mixing of the liquids in the receptacles 28 and 51 is effected by opening the valve 63. By virtue of the receptacle 65, only 50 cm$^3$ of the 500 cm$^3$ produced are collected. By then opening the valves 64 and 67, the liquids in the receptacles 65 and 52 are mixed in the tube 60, whereby a sample which is diluted to one hundredth is obtained at the discharge from the tube.

It will be appreciated that many alternative forms of the invention are possible. Thus, without departing from the scope of the invention, it will be possible to use any suitable system other than that which has been specifically described for filtering the slurry of the mixture.

Moreover, it will be apparent that the diluting apparatus shown in FIG. 2 could be modified by the provision of a series of diluting water receptacles comprising more than two receptacles and respectively discharging into a series of a plurality of mixer tubes, while the latter may or may not be separated from each other by intermediate receptacles. That aspect depends upon the dilution effect required.

Referring to FIG. 3, it is also possible to provide a diluting system with a metering or peristaltic pump 80, an intake of which would be connected to the outlet of the chamber 6, while the other intake or intakes would be connected to a diluting liquid tank 82 and would receive the required flow of such liquid.

Referring to FIG. 4, it is possible to provide dilution for automatic syringes or pipettes 84, one of the syringes or pipettes pipetting the sample collected and the other the diluting liquid.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. An apparatus for withdrawing a liquid sample from a particulate solid containing liquid medium, comprising:
    a collection assembly constructed and arranged for insertion into a particulate solid containing liquid medium, and comprising means for filtering a liquid fraction from such a medium and collection chamber means for receiving a liquid fraction filtered by said filtering means;
    first chamber means for receiving liquid;
    first means for communicating said first chamber means with said collection chamber means;
    second chamber means for receiving sample liquid;
    second means for communicating said second chamber means with said collection chamber means, said first and second communicating menas separate of each other so that said first and second chamber means are in parallel flow relationship to each other, said first and second communicating means including separate orifices independently open to said collection chamber means;
    first means for selectively drawing liquid fraction from said collection chamber into said first chamber means through said first communicating means;
    second means for selectively drawing liquid fraction from said collection chamber into said second chamber means through said second communicating means, said first and second selectively drawing means operable independently of each other so that liquid fraction may be first drawn into said first chamber means without liquid fraction being drawn into said second chamber means;
    first means for selectively discharging drawn liquid from said first chamber means; and
    second means for selectively discharging drawn sample liquid from said second chamber means.

2. The apparatus as defined by claim 1 wherein said collection chamber means includes a conically walled housing having an apex end and a base end with an opening, and wherein said filtering means is positioned at said opening.

3. The apparatus as defined by claim 2, wherein said first selectively communicating means includes a first conduit having an end portion positioned in said housing at said apex end.

4. The apparatus as defined by claim 1, wherein said second drawing means defines means for drawing liquid fraction from said collection chamber into said second chamber means through said second communicating means without interrupting said first drawing means.

5. The apparatus as defined by claim 1, further comprising first and second means for selectively delivering water to said first and second chamber means, respectively.

6. The apparatus as defined by claim 5, further comprising means for selectively delivering compressed air to said first and second chamber means, respectively.

7. The apparatus as defined by claim 3, wherein said second selectively communicating means includes a second conduit having an end portion positioned in said housing at a location intermediate of said apex and base ends.

8. The apparatus as defined by claim 7, wherein said second selectively drawing means includes valve means at a location along said second communicating means, said first communicating means being valveless so as to be continuously open, whereby said second drawing means is operable without interruption of said first drawing means.

9. The apparatus as defined by claim 8, wherein said collection chamber means is arranged for insertion into a liquid/solids medium with said apex end disposed above said filtering means.

10. The apparatus as defined by claim 1, wherein said second selectively drawing means includes valve means at a location along said second communicating means, said first communicating means being valveless so as to be continuously open.

11. The apparatus as defined by claim 10, wherein said first selectively discharging means discharges liquid from said first chamber means through said first communicating means.

12. The apparatus as defined by claim 11, wherein said first selectively drawing means includes a first vacuum line communicated with said first chamber means and said second selectively drawing means includes a second vacuum line communicated with said second chamber means.

13. The apparatus as defined by claim 1, further comprising means for diluting sample liquid discharged from said second chamber means.

14. The apparatus as defined by claim 13, wherein said dilution means includes a metering or peristaltic pump and means for communicating an intake of said pump with said means for selectively discharging contents of said second chamber means, a source of diluting liquid and means for communicating an intake of said pump with said source of diluting liquid.

15. The apparatus as defined by claim 13, said dilution means comprising means for pipetting liquid sample and diluting liquid.

16. The apparatus as defined by claim 13, wherein said dilution means comprises a calibrated first receptacle in communication with said means for selectively discharging sample liquid from said second chamber, at least one mixing container, a receiving container, means for selectively discharging contents of said first receptable into said mixing container, means for discharging contents of mixing container into said receiving container, at least one calibrated second receptacle, means for selectively supplying water to said second receptacle and means for selectively discharging contents of said second receptacle into said mixing container.

17. The apparatus as defined by claim 16, further comprising cleaning means for selectively introducing cleaning fluid into said calibrated second receptacle.

18. The apparatus as defined by claim 1 wherein said first and second means for selectively delivering water to said first and second chamber means each include a conduit constructed and arranged to tangentially introduce water into the respective one of said first and second chamber means and wherein said means for selectively discharging contents of said first receptacle includes a conduit constructed and arranged to tangentially discharge said receptacle contents into said mixing container.

19. The apparatus as defined by claim 16, wherin all said selectively communicating means, said selectively discharging means, said selectively delivering means, and said valve means each include electrically actuated valves, said apparatus further comprising a programmer for selectively actuating members of said valves automatically.

20. The apparatus as defined by claim 16, wherein said diluting means includes a plurality of mixing containers, means for communicating said mixing containers in series, a plurality of calibrated second receptacles and a plurality of menas for selectively communicating each member of said plurality of second receptacles with a different member of said plurality of mixing containers.

* * * * *